United States Patent [19]
Harmalker et al.

[11] Patent Number: 6,150,313
[45] Date of Patent: Nov. 21, 2000

[54] SKIN CLEANSING COMPOSITION COMPRISING A MIXTURE OF THICKENING POLYMERS

[75] Inventors: Subhash Harmalker, Somerset; Gail Klewsaat, Neshanic Station; Tracey Aldrich, Somerset, all of N.J.

[73] Assignee: Colgate-Palmolive Company, New York, N.Y.

[21] Appl. No.: 09/375,753

[22] Filed: Aug. 18, 1999

[51] Int. Cl.$^7$ ................ C11D 3/37; C11D 3/18; C11D 1/72

[52] U.S. Cl. .......... 510/130; 510/119; 510/121; 510/122; 510/130; 510/151; 510/208; 510/230; 510/242; 510/251; 510/361; 510/398; 510/400; 510/417; 510/421; 510/466; 510/533

[58] Field of Search .................. 510/119, 121, 510/122, 130, 151, 208, 242, 251, 398, 400, 417, 421, 466, 230, 361, 533

[56] References Cited

U.S. PATENT DOCUMENTS

| | | | |
|---|---|---|---|
| 5,409,640 | 4/1995 | Giret et al. | 252/546 |
| 5,726,138 | 3/1998 | Tsaur et al. | 510/158 |
| 5,942,479 | 8/1999 | Frankenbach et al. | 510/159 |
| 5,965,115 | 10/1999 | Bolich, Jr. et al. | 424/70.12 |
| 5,972,356 | 10/1999 | Peffly et al. | 424/401 |
| 5,985,294 | 11/1999 | Peffly | 424/401 |

FOREIGN PATENT DOCUMENTS 9716168  5/1997  WIPO .

OTHER PUBLICATIONS

B.F. Goodrich, Carbopol Water Soluble Resins, 1–36, Sep. 1987.
Rohm and Haas, Aculyn Personal Care Polymers, 1996, 1–16.
ICI, Products for Personal Care, 1996, 1–7.

*Primary Examiner*—Yosendra Gupta
*Assistant Examiner*—Charles Boyer
*Attorney, Agent, or Firm*—Martin B. Barancik

[57] ABSTRACT

An aqueous composition comprising
a. a skin cleansing effective amount of a surfactant or mixture thereof;
b. a silicone in quantities of from about 0.1 to about 8 wt. % of the composition;
c. a hydrocarbonaceous material in quantities of from about 0.1 to about 8 wt. % of the composition;
d. a cationic polymer in quantities of from about 0.02 to about 1 wt. % of the composition;
e. a combination of a polyacrylate thickening polymer and an acrylate methacrylate copolymer wherein the ester group of the methacrylate is alkyl of about 12 to about 20 carbon atoms, said alkyl having about fourteen to about twenty six ethoxy groups and the acrylate is one or more monomers of acrylic acid, methacrylic acid or one of their simple esters in quantities sufficient to provide both viscosity and visual phase stabilization; and
f. the balance water.

24 Claims, No Drawings

SKIN CLEANSING COMPOSITION COMPRISING A MIXTURE OF THICKENING POLYMERS

BACKGROUND OF THE INVENTION

Basic skin cleansing activities have been long addressed by the personal care industry. Removing soil from the skin is a worldwide requirement of the consumer population that has been met by the available skin cleansing products. The consumer population is now looking for additional benefits beyond basic cleansing. Skin conditioning i.e. smoothness, texture, etc., is a desired characteristic and brought about through the presence of emollients in a basic skin cleansing composition. Additionally, the presence of components which bring about an antibacterial effect on the skin arc now becoming ever more acceptable and desirable by the consumer population.

Delivering a benefit to the skin other than cleansing during the cleansing process has been receiving increasing attention in the last few years. For example, the disclosure of dual compartment delivery systems to deliver benefit agents to the skin as well as larger sized droplets of the benefit agent are now known. However, in order to achieve these results the composition must be compatabilized, as assessed by stability parameters over a period of time and a range of temperatures. Such parameters include maintenance and stabilization of viscosity and as a further measure the establishment and desired maintenance of visual phase integrity. These parameters are particularly significant for liquid compositions wherein the large quantity of water make the establishment of a stable composition more difficult, particularly when substantially water insoluble benefit agents are dispersed in water and desirably form an emulsion, more desirably an oil in water emulsion.

It has now been found that a liquid aqueous composition suitable for cleansing the skin and comprising a. a skin cleansing effective amount of a surfactant or mixtures thereof;
b. a silicone;
c. a hydrocarbonaceous material;
d. a cationic polymer; and
e. the balance water can be successfully stabilized with respect to viscosity by the addition of a combination of a polyacrylate thickening polymer and an acrylates/methacrylate copolymer wherein the ester group of the methacrylate is alkyl of about 12 to about 20 carbon atoms and having about fourteen to about twenty six ethoxy groups and the acrylate is one or more monomers of acrylic acid, methacrylic acid or one of their simple esters. An example of the first polymer is Aculyn 33®, a polymer also marketed by Goodrich. An example of the second polymer is Aculyn 22®, a polymer also marketed by Goodrich.

The use of the two phase stabilizers, i.e., the acrylates copolymer e.g., Aculyn 33 and the long chain ethoxylated ester methacrylate copolymer, e.g., Aculyn 22 provides a tight stable multi-phased composition over a reasonable range of variables. However, for further stabilization, particularly at high temperatures, it is desirable to utilize a further phase stabilization component. This material is generally a polyacrylic acid lightly to moderately crosslinked with an allylic ether(s) of polyol(s) such as pentaerythritol, sucrose or propylene and the like. These materials are sometimes known generally as "Carbopols". The one that appears most desirable for the complex system of this application is Carbomer 934® available from B. F. Goodrich or 3V Inc.

Although not necessary to be present in the stabilized composition, a further component which is desirable with the first two polymer systems, as well as the two polymer systems plus the cross lined polyacrylic acid is a long chain ethoxylated primary alcohol. Generally the alcohol is alkyl or alkenyl, preferably alkyl, having about ten to about twenty carbon atoms and about one to about four ethoxy groups. Steareth-2 is a desirable compound. The presence of these materials brings about a highly stable emulsion.

The stabilization of this silicone, hydrocarbonaceous, particularly petrolatum emulsion, is complex and complicated due to the necessary presence of the two nonaqueous water insoluble components—silicone and hydrocarbonaceous component. These materials appear to operate independently and can form separate dispersed drops of significantly different sizes. Through the stabilization system of this invention an emulsion can be prepared which does not readily break apart, and is temperature and shear stable and maintains itself at a relatively high temperature over a significant period of time.

The desired composition is both stabilized as to viscosity and visual phase integrity with the polyacrylate thickening polymer (Aculyn 33 as example) and the acrylate methacrylate copolymer (Aculyn 22 as example). Since neither one of these two agents alone stabilize the composition at the quantities employed for each alone, there may be an unknown interaction occurring among the composition components. The usage of these two agents together bring about a composition which maintains viscosity integrity over a specific period of time and a wide temperature range.

SUMMARY OF THE INVENTION

In accordance with the invention there is a liquid aqueous composition suitable for skin cleansing comprising a. a skin cleansing effective amount of a surfactant or mixture thereof;
b. a silicone in quantities of from about 0.1 to about 8 wt. % of the composition;
c. a hydrocarbonaceous material in quantities of from about 0.1 to about 8 wt. % of the composition;
d. a cationic polymer in quantities of from about 0.02 to about 1 wt. % of the composition;
e. a combination of a polyacrylate thickening polymer and an acrylate methacrylate copolymer wherein the ester group of the methacrylate is alkyl of about 12 to about 20 carbon atoms, said alkyl having about fourteen to about twenty six ethoxy groups and the acrylate is one or more monomers of acrylic acid, methacrylic acid or one of their simple esters in quantities sufficient to provide both viscosity and visual phase stabilization; and
f. the balance water.

Additionally, there is a composition comprising components a to f above together with at least one additional component, "g", a polyacrylic acid lightly to moderately crosslinked with an allylic ether(s) of a polyol(s) or propylene as previously mentioned. This is particularly advantageous for higher temperature phase stabilization.

Still further, an additional component, "h", can be added to the composition having the components of "e", therein, and more desirably to the composition having the "g" component as well as the two "e" components. This is a long chain ethoxylated primary alcohol. Generally the alcohol is alkyl or alkenyl, preferably alkyl having about twelve to about 20 carbon atoms and about 1 to about 4 ethoxy groups. Steareth-2 is desirable. The presence of "h" brings about a highly stable emulsion.

DETAILED DESCRIPTION OF THE INVENTION

The desired composition will have both appropriate stabilized viscosity and visual phase stability.

In line with the cleansing activity of the composition, there is a skin cleansing effective amount of a surfactant present in the composition. Soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition.

Other surfactants can be present in the composition as well. Examples of such surfactants are the anionic, amphoteric, nonionic and cationic surfactants. Examples of anionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

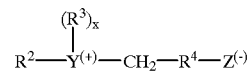

wherein $R^2$ contains an alkyl, alkenyl, or hydroxy alkyl radical of from about 8 to about 18 carbon atoms, from 0 to about 10 ethylene oxide moieties and from 0 to I glyceryl moiety; Y is selected from the group consisting of nitrogen, phosphorus, and sulfur atoms; R3 is an alkyl or monohydroxyalkyl group containing 1 to about 3 carbon atoms; X is I when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;

laurylpyridinium chloride;
cetylpyridinium chloride
lauryipyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

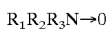

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexa-decylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethyl-phosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

Each of the families of surfactants disclosed above—anionic, zwitterionic, amphoteric, nonionic and cationic—can be specifically omitted from the composition, as well as any specific surfactant of each family of surfactants.

Silicone as used herein is preferably a silicone fluid, as opposed to a silicone gum. A silicone fluid is defined herein as silicone with viscosities ranging from about 5 to about 600,000 centistokes, more preferably from about 350 to about 100,000 centistoke at 25° C. Polyalkyl siloxanes such as polydimethyl siloxane, are preferred for use as the silicone.

The silicone materials useful in the present invention are generally non-volatile and may be either a polyalkyl siloxane, a polyaryl siloxane, a polyalkylaryl siloxane, a functionalized siloxane, such as a polysiloxane with amino functional substitution, an alkoxylated silicone, such as ethoxylated or propoxylated, and a polyether siloxane copolymer. The silicones useful in the present invention may be endcapped with any number of moieties, including, for example, methyl, hydroxyl, ethylene oxide, propylene oxide, amino, trialkyl silane (preferably methyl), carboxyl, and the like. Mixtures of these materials may also be used and are preferred in certain implementations. Additionally, volatile silicones may be used as part of the silicone mixture so long as the final mixture is at least essentially non-volatile.

The polyalkyl silicones that may be used herein include, for example, polydimethyl siloxanes with viscosities ranging from about 5 to about 600,000 centistokes at 25° C. preferably a minimum amount of about 150 or 200 centistokes. These siloxanes are available, for example, from General Electric Company as the Viscasil series and from Dow Corning as the Dow Coming 200 series. The viscosity can be measured by means of a glass capillary viscosmeter as set forth in Dow Coming Corporate Test Method CTM0004, Jul. 20, 1970. Preferably the viscosity ranges from about/50 centistokes to about 150,000 centistokes and most preferably from about 350 centistokes to about 100,000 centistokes. Silicone gums that is, silicones with viscosities above about 600,000 centistokes are desirably essentially absent or totally absent from the compositions. However, a combination of a lower viscosity silicone together with a silicone gum can being about a material with reasonable handling characteristics together with good deposition and skin conditioning.

The polyalkylaryl silicones that may be used include, for example, polymethylphenylsiloxanes having viscosities of from about 15 to about 65 centistokes at 25° C. These siloxanes are available, for example, from the General Electric Company as SF 1075 methyl phenyl fluid or from Dow Coming as 556 Cosmetic Grade Fluid. Additionally, poly(dimethyl siloxane) (diphenyl siloxane) copolymers having a viscosity in the range of from about 10 to about 100,000 centistokes at 25° C. are useful. The polyether siloxane copolymer that may be used is, for example, a polypropylene oxide modified dimethylpolysiloxane (e.g., Dow Corning DC-1248, although ethylene oxide or mixtures of ethylene oxide and propylene oxide may also be used.

References disclosing suitable silicones include U.S. Pat. No. 2,826,551, issued Mar. 11, 1958; Green; U.S. Pat. No. 3,964,500, issued Jun. 22, 1967, Drakoff; U.S. Pat. No. 4,364,837, issued Dec. 21, 1982, Pader; and British Patent No. 849,433, Wooston, published Sep. 28, 1960. All of these patents are incorporated herein by reference. Also incorporated herein by reference is Silicon Compounds, distributed by Petrarch Systems, Inc., 1984. This reference provides a good listing of suitable silicone material.

Component c can be a typical hydrocarbonaceous material such as a wax, petrolatum, mineral oil, beeswax, a "permethyl" made up of longer chain branched hydrocarbons available from Permethyl Corporation. Permethyls are of the general formula

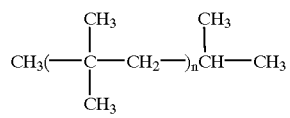

where n can vary from about 4 to over 200. Products where n=4, 16, 38, 214, respectively, are marketed as Permethyl 102A, 104A, 106A and 1082A.

Additional hydrocarbonaceous material which can be employed include lanolins and lanoleic like materials such as long chain alkyl esters and ethers of the lanolins.

The petrolatum useful in the present invention can be any grade of white or yellow petrolatum recognized in the art as suitable for human application. Preferred petrolatum are those with a melting point in a range of from about 35° C. to about 70° C., preferably about 50 to 60° C. The petrolatum of the composition can include hydrocarbon mixtures formulated with mineral oil and/or in combination with paraffin waxes of various melting points; all in small quantities compared to the petrolatum. A petrolatum without additional materials is preferred. Examples of waxes, particularly useful in solid compositions are microcrystalline waxes, generally those waxes which are known as paraffin wax, beeswax, and natural waxes derived from vegetables, shea wax and the like.

Cationic polymers is that generic class of materials which generally provide a positive skin feel to the skin during cleansing application, rinse off, and thereafter.

Cationic polymers includes but are not limited to the following groups:

(I) cationic polysaccharides;

(II) cationic copolymers of saccharides and synthetic cationic monomers, and (III) synthetic polymers selected from the group consisting of:
  (a) cationic polyalkylene imines
  (b) cationic ethoxy polyalkylene imines
  (c) cationic poly[N-[3-(dimethylammonio)propyl]-N'[3-(ethyleneoxy-ethylene dimethylammonio)propyl] urea dichloride]
  (d) in general a polymer having a quaternary ammonium or substituted ammonium ion.

The cationic polysaccharide class encompasses those polymers based on 5 or 6 carbon sugars and derivatives which have been made cationic by engrafting of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactommannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomannans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4-β; 1,3-α; 1,3-β and 1,6 linkages. The synthetic cationic monomers for use in these copolymers can include dimethyldiallylammonium chloride, dimethylaminoethylmethyacrylate, diethyldiallylammonium chloride, N,N-diallyl,N-N-dialklyl ammonium halides, and the like. A preferred cationic polymer is Polyquatemium 7 prepared with dimethyldiallylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkelene imines, and poly{N-[3-(dimethylammonio)-propyl]-N'-[3-(ethyleneoxyethylene dimethylammoniumo)propyl]urea dichloride] the latter of which is available form Miranol Chemical Company, Inc. under the trademark of Miranol A-15, CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized guars and guar gums and the like. Exemplary of cationic polymers which can be used to make the complexes of this invention include, as disclosed in the CTFA International Cosmetic Ingredient Dictionary (Fourth Edition, 1991, pages 461–464); Polyquaternium -1,-2,-4 (a copolymer of hydroxyethylcellulose and diallyldimethyl ammonium chloride), -5 (the copolymer of acrylamide and betamethacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers, -8 (the polymeric quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethylmethacrylate), -12 (a polymeric quaternary ammonium salt prepared by the reaction of ethyl meth acrylate/abietyl methacrylate/diethylaminoethyl methacrylate copolymer with dimethyl sulfate), -13 (a polymeric quaternary ammonium salt prepared by the reaction of ethyl methacrylate/oleyl methacrylate/diethylaminoethyl methacrylate copolymer with dimethyl sulfate), -14,-15 (the copolymer of acrylamide and betamethacrylyloxyethyl trimethyl ammonium chloride), -16 (a polymeric quaternary ammonium salt formed from methylvinylimidazolium chloride and vinylpyrrolidone), -17,-18,-19 (polymeric quaternary ammonium salt prepared by the reaction of polyvinyl alcohol with 2,3-epoxy-propylamine), -20 (the polymeric quaternary ammonium salt prepared by the reaction of polyvinyl octadecyl ether with 2,3-epoxypropylamine), -22,-24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquaternium-17 (q.v.)), -28,-29 (is Chitosan (q.v.) that has been reacted with propylene oxide and quaternized with epichlorohydrin), and -30.

The quantity of water present in the composition is substantial. Generally, at least about 60 wt. % of the composition is water, usually at least about 70 wt. %, and often times at least about 80 wt. % of the composition is water. This large quantity of water together with a significant quantity of a difficult to solubilize organic like moiety such as silicone particularly together with the hydrocarbonaceous material, for example, petrolatum, creates a system which is highly unstable as measured by such parameters as visible examination of phases and viscosity.

Through the use of a combination of a polyacrylate thickening polymer and an acrylate methacrylate copolymer as generally disclosed as component "e" of the inventive composition, a viscosity stabilized compatibilized gelled composition is obtained.

The surfactant level in the aqueous liquid composition is any level, which can create foaming upon agitation when applied to the skin. Generally, this is a minimum of about 1 wt. % of the composition, generally, at least about 2 wt. % of the composition and preferably at least about 3, 4 or 5 wt. % of the composition. Generally, not more than about 30 wt. % of the composition is surfactant, although generally it is not more than about 25 or 20 wt. % of the composition. Preferably, no more than about 17 wt. % of the composition is surfactant. One or a mixture of surfactants can be employed. Generally, at least some of the surfactant is an anionic surfactant such as alkyl sulfate, ethoxylated alkyl sulfate, alpha olefin sulfonate or other mild surfactants, for example, taurates, phosphates and the like.

The quantity of silicone is generally from about 0.1 to about 8 wt. % of the composition, preferably from about 0.5 to about 5 wt. % of the composition, more desirably about 1 to 3 wt. % of the composition. The average particle size of the silicone is generally below about 50 microns, desirably below about 35 microns. A minimum average particle size is generally above about 2 microns, desirably above about 5 microns.

The quantity of hydrocarbonaceous material is from about 0.1 to about 8 wt. % of the composition, preferably about 0.5 to about 5 wt. %, desirably about 1 to about 4 wt. %. The hydrocarbonaceous material is preferably a petrolatum as identified above. The average particle size of the petrolatum can vary and is not unduly significant but is generally below about 25 microns, desirably below about 20 or even 10 microns. Generally, the minimum average particle size is above about 1 microns, or above about 2 microns.

The particle size of the silicone and petrolatum are volume particle size as measured by light scattering methods such as utilized by a Coulter LS 130 apparatus.

The cationic polymer is present from about 0.02 to about 1.0 wt. % of the composition, preferably about 0.05 to about 0.8 wt. % of the composition. Lower quantities can be employed, for example up to about 0.5 wt. % or up to about 0.4 wt.

The stability of the gelled phase and therefore the viscosity of the composition is maintained by the presence of the identified polymer systems of component "e" previously mentioned.

The first polymer is a copolymer comprised of two or more monomers comprising acrylic acid, methacrylic acid, or one of their simple esters including methyl, ethyl, or propyl. Light cross linking can also be present within the molecule. Activation of the molecule is caused by reacting with base such as sodium hydroxide to a pH between about 6 and 9 thereby forming the salt of the acid where appropriate. The second polymer is an acrylate methacrylate copolymer wherein the acrylate is one or more monomers of acrylic acid, methacrylic acid or one of their simple esters such as methyl, ethyl or propyl and the methacrylate portion has an ester group of methacrylate which is alkyl of about 12 to about 20 carbon atoms, said alkyl having about fourteen to about twenty six ethoxy groups. Activation of the molecule occurs in the same manner as with Aculyn 33 thereby forming the salt of the acid where appropriate.

The quantity of each of the polymer systems present in the composition is together sufficient to stabilize the system with respect to gellation and therefore its viscosity. This can be measured by its stability at various times and temperatures. Various combinations of quantities of the two polymer systems can be employed and it is somewhat difficult to fix absolute minimal and maxima. However, in general, the first polymer is present in the composition at a minimum of about 0.5, or about 0.75, preferably about 1.0 wt. % of the aqueous composition. The second polymer is present in the composition at a minimum of about 0.1 wt. % or about 0.2 wt. %, preferably about 0.5 wt. % of the composition. As a general rule, the maximum quantities of the polymers are related to observable adverse effects present in the system such as too high a viscosity. Still further, when a smaller quantity of one polymer is used, in general a medium to relatively large quantity of the second polymer can be employed. However, in general, a maximum of about 2 wt. % preferably about 1.0 wt. % of the composition of the first polymer can be employed. A maximum of about 1.0 wt. % preferably about 0.5 wt. % of the composition of the second polymer can be employed. As stated previously neither polymer alone with repeat stabilizing of the system. Therefore, a substantial excess of either polymer to the other should generally be avoided.

With respect to viscosity, there can be some viscosity variation over the evaluated time and temperature range; however, this should be within normal expected and accepted variation for the desired viscosity. The viscosity of the composition should be one which is readily dispersible from a container by pouring, deforming the sides, or hand pumpable. Viscosity from about 1,000 to about 40,000 centipoise, preferably about 1,500 to about 30,000 centipoise can be employed more desirably about 2,000 to about 20,000 and most desirably about 4,000 to about 17,000 centipoise. Viscosities up to about 20,000 are measured on a Brookfield DVII+Viscometer using a number 5 spindle at 20 rpm and 25° C. Viscosities above about 20,000 centipoise are measured on that Viscometer using a number 7 spindle at 20 rpm and 25° C.

The preparation and maintenance of a stable emulsion in this system is particularly desirable. If not appropriately mixed and the phases maintained, the true benefit of the nonaqueous components cannot be properly achieved. Of particular significance is the higher temperature stability of the stabilized system. It has been found that it is desirable to add a third polymeric component to the stabilization system. The aforementioned component "g: is a homopolymer of polyacrylic acid which is generally lightly to moderately crosslinked with an allylic ether(s) of a polyol such as pentacrythritol, sucrose or propylene and the like. Activation of the molecule is caused by reaction with a base to a pH between about 6 and 9 thereby forming the salt of the acid where appropriate. Generally the polyol has about four to about twelve hydroxy groups. The molecular weight range of these polyacrylatic acids is generally from about $2\times10^6$ to less than about $4\times10^6$ weight average, more desirably about $2.5\times10^6$ to about $3.5\times10^6$. The quantity of polymer present in the composition is generally about 0.05 wt. % to about 1.0 wt. % of the composition, more desirably about 0.1 wt. % to about 0.6 wt. %.

A further component which can be in the composition, the aforementioned component "h" like component "g" also need not be present but which is desirably present is a long chain ethoxylated primary alcohol. Generally the alcohol is alkyl or alkenyl, preferably alkyl, having about ten to about twenty carbon atoms and about one to about four ethoxy groups. Steareth-2 is a desirable compound. The presence of these materials brings about a highly stable emulsion. The quantity of long chain alcohol in the composition is enough to provide a highly stable emulsion. Generally at least about 0.05 wt. %, desirably about 0.1 wt. % of the composition can be used. The maximum quantity is dependent upon emulsion stability and desired composition viscosity. Generally no more than about 0.5, desirably no more than about 0.4 wt. % is employed.

This further additional component helps bring about a highly stable emulsion.

Stability as measured by visual inspection at a temperature of 120° F. for four weeks is significant. Alternatively visual inspection stability at 110° F. for thirteen weeks is also an acceptable time period.

The composition of the invention appears to provide protection to the skin, even as a wash off product. Examples of such protection include but are not limited to less prevalence of a dye on the skin after administration methods. Increased skin moisturization also occurs. Additionally, any fragrance present in the composition may be longer lasting on the skin.

The compositions of the invention are made by standard techniques well known in the art. For example, the water soluble materials such as surfactants are combined together with water, generally de-ionized, and mixed at an elevated temperature of about at least 50° C. preferably above about 70° C. The water insoluble materials are then mixed together in a separate vessel, for example, the petrolatum, dimethicone, emulsifier, stabilizing copolymer (Carbomer 934), and water insoluble emollients if present at an elevated temperature for example 50° C. The water-soluble and water insoluble materials are mixed at elevated temperature, preferably at 70° C., or higher, for about 30 minutes. A solution of alkaline materials like sodium hydroxide, and EDTA in water, in an amount necessary to obtain the final pH of about 6–7, more preferably, about 6.25 to 6.75, is added to the above product and mixed. The other two copolymers (Aculyn 22 and 33) are pre-mixed with equal amount of water and are then added to the above product and mixed for about 30 minutes. The cationic polymer, for example, (Polyquat) is then added to the batch while mixing. It is then cooled down to about 40 deg. C before adding the fragrance.

The product is then cooled down to room temperature and the viscosity is lowered if desired to a specific level by adding a polyoxyethylene plus polyoxypropylene copolymer such as poloxamer 124.

EXAMPLES

Below are examples of the invention. This example is intended to illustrate but not unduly limit the invention.

Examples 1 and 2

Following the standardized procedure, the formulations set forth below are prepared.

| Component | Example 1 wt. % | Example 2 wt. % |
| --- | --- | --- |
| Sodium laureth(2) sulfate | 8.2 | 7.5 |
| Cocoamidopropylbetaine | 3.0 | 3.0 |
| Laurylpolyglycoside | 1.12 | 1.12 |
| Acrylate/steareth - 20 Methacrylate copolymer (aculyn 22) | 0.45 | 0.45 |
| Acrylates Copolymer (aculyn 33) | 0.84 | 0.84 |
| Petrolatum | 2.0 | 2.0 |
| Dimethylpolysiloxane (60,000 cps) | 1.0 | 1.0 |
| Sodium Chloride | 0.5 | 0.6 |
| Carbopol (carbomer 934) | 0.2 | 0.4 |
| Steareth - 2 | 0.1 | 0.1 |
| Polyquat-7 | 0.2 | 0.2 |
| Poloxamer 124 | 0.33 | 0.1 |
| Fragrance | 0.8 | 0.2 |
| Preservative, base, chelating agents, others | 0.5 | 1.2 |
| Water | Balance | Balance |

Example 1 has a pH of about 6.5 and a viscosity of about 5,250 cps at 25° C. using spindle 5 at 20 rpm on a Brookfield RVD II+viscometer. Example 2 has a pH of about 6.5 and a viscosity of about 14,500 cps at 25° C. using spindle 5 tat 20 rpm on a Brookfield RVD II+viscometer.

What is claimed is:

1. An aqueous composition comprising
   a. a skin cleansing effective amount of a surfactant or mixture thereof;
   b. a silicone in quantities of from about 0.1 to about 8 wt. % of the composition;
   c. a hydrocarbonaceous material in quantities of from about 0.1 to about 8 wt. % of the composition;
   d. a cationic polymer in quantities of from about 0.02 to about 1 wt. % of the composition;
   e. a combination of a polyacrylate thickening polymer and an acrylate methacrylate copolymer wherein the ester group of the methacrylate is alkyl of about 12 to about 20 carbon atoms, said alkyl having about fourteen to about twenty six ethoxy groups and the acrylate is one or more monomers of acrylic acid, methacrylic acid or one of their simple esters in quantities sufficient to provide both viscosity and visual phase stabilization; and
   f. the balance water.

2. The composition in accordance with claim 1 wherein the surfactant or mixture thereof is at least about 1 wt. % of the composition.

3. The composition in accordance with claim 2 wherein the surfactant or mixture thereof is no more than about 25 wt. % of the composition.

4. The composition in accordance with claim 1 wherein the silicone is about 0.5 to about 5 wt. % of the composition.

5. The composition in accordance with claim 1 wherein the hydrocarbonaceous component is petrolatum and it is present in the composition at about 0.5 wt. % to about 5 wt. %.

6. The composition in accordance with claim 1 wherein the cationic polymer is about 0.05 wt. % to about 0.8 wt. % of the composition.

7. The composition in accordance with claim 3 wherein the silicone is about 0.5 wt. % to about 5 wt. % of the composition, the hydrocarbonaceous component is petrolatum and is about 0.5 wt. % to about 5 wt. % of the composition and the cationic polymer is about 0.05 wt. % to about 0.8 wt. % of the composition.

8. The composition in accordance with claim 1 wherein the polyacrylate thickening polymer is about 0.5 wt. % to about 2.0 wt. % of the composition.

9. The composition in accordance with claim 1 wherein the acrylate copolymer methacrylate copolymer is about 0.1 wt. % to about 1.0 wt. % of the composition.

10. The composition in accordance with claim 8 wherein the acrylate methacrylate copolymer is about 0.1 wt. % to about 1.0 wt. % of the composition.

11. The composition in accordance with claim 7 wherein the polyacrylate thickening polymer is about 0.5 wt. % to about 2.0 wt. % of the composition and the acrylate methacrylate copolymer is about 0.1 to about 1.0 wt. % of the composition.

12. The composition in accordance with claim 1 wherein a polyacrylic acid lightly to moderately crosslinked polymer is present in high temperature stabilizing quantities of the composition.

13. The composition in accordance with claim 1 wherein a primary long chain alkyl or alkenyl ethoxylated alcohol is present in the composition in emulsion stabilizing quantities.

14. The composition in accordance with claim 12 wherein a primary long chain alkyl or alkenyl ethoxylated alcohol is present in the composition in emulsion stabilizing quantities.

15. The composition in accordance with claim 12 wherein the crosslinked polyacrylic acid is about 0.05 to about 1.0 wt % of the composition.

16. The composition in accordance with claim 13 wherein the alcohol is about 0.05 to about 0.5 wt % of the composition.

17. The composition in accordance with claim 15 wherein the alcohol is about 0.05 to about 0.5 wt % of the composition.

18. The composition in accordance with claim 11 wherein a polyacrylic acid lightly to moderately crosslinked is present in the composition in about 0.05 to about 1.0 wt % of the composition.

19. The composition in accordance with claim 11 wherein a primary long chain alkyl or alkenyl ethoxylated alcohol is present in about 0.05 to about 0.5 wt % of the composition.

20. The composition in accordance with claim 19 wherein a polyacrylic acid lightly to moderately crosslinked is present in the composition in about 0.05 to about 1.0 wt % of the composition.

21. The composition in accordance with claim 20 wherein the alcohol has alkyl of about 10 to about 20 carbon atoms and about 1 to about 4 ethoxy groups.

22. The composition in accordance with claim 7 wherein a polyacrylic acid lightly to moderately crosslinked polymer is present in high temperature stabilizing quantities of the composition.

23. The composition in accordance with claim 7 wherein a long chain primary alkyl or alkenyl ethoxylated alcohol is present in the composition in emulsion stabilizing quantities.

24. The composition in accordance with claim 22 wherein a long chain primary alkyl or alkenyl ethoxylated alcohol is present in the composition in emulsion stabilizing quantities.

* * * * *